(12) United States Patent
Ling et al.

(10) Patent No.: US 11,873,286 B2
(45) Date of Patent: Jan. 16, 2024

(54) METHOD FOR PREPARING 2,5-FURANDICARBOXYLIC ACID (FDCA) FROM FURFURAL

(71) Applicant: Shanghai Wokai Biotechnology Co., Ltd., Shanghai (CN)

(72) Inventors: Fang Ling, Shanghai (CN); Ruming Feng, Shanghai (CN); Yong Feng, Shanghai (CN); Haiquan Ding, Shanghai (CN)

(73) Assignee: SHANGHAI WOKAI BIOTECHNOLOGY CO., LTD., Shanghai (CN)

( * ) Notice: Subject to any disclaimer, the term of this patent is extended or adjusted under 35 U.S.C. 154(b) by 0 days.

(21) Appl. No.: 18/218,128

(22) Filed: Jul. 5, 2023

(65) Prior Publication Data

US 2023/0382882 A1 Nov. 30, 2023

Related U.S. Application Data

(63) Continuation of application No. PCT/CN2022/107071, filed on Jul. 21, 2022.

(30) Foreign Application Priority Data

May 27, 2022 (CN) .......................... 202210594101.0

(51) Int. Cl.
*C07D 307/68* (2006.01)

(52) U.S. Cl.
CPC .................................. *C07D 307/68* (2013.01)

(58) Field of Classification Search
CPC ..................................................... C07D 307/68
See application file for complete search history.

(56) References Cited

FOREIGN PATENT DOCUMENTS

| | | |
|---|---|---|
| CN | 107325065 A | 11/2017 |
| CN | 108017602 A | 5/2018 |
| CN | 110437190 A | 11/2019 |
| CN | 114773300 A | 7/2022 |
| WO | 2015056270 A1 | 4/2015 |

*Primary Examiner* — Golam M Shameem
(74) *Attorney, Agent, or Firm* — Bayramoglu Law Offices LLC

(57) ABSTRACT

A method for preparing FDCA with furfural as a raw material includes (1) pretreatment of the furfural: subjecting the furfural and an alcohol compound to an acetalization reaction under catalysis of an acidic ion resin to obtain an acetal compound of the furfural with the alcohol compound; (2) under stirring, adding the acetal compound dropwise to a mixed liquid of an acylation reagent and an ionic liquid (IL) to allow a reaction for 1 h to 2 h, adding a catalyst to continue the reaction for 3 h to 5 h, and subjecting a resulting reaction system to a post-treatment to obtain 5-acylfurfural; and (3) mixing the 5-acylfurfural with hydrogen peroxide, adding a catalyst to allow an oxidation reaction, and after the oxidation reaction is completed, subjecting a product to washing and recrystallization to obtain a white crystal, which is the FDCA.

10 Claims, No Drawings

METHOD FOR PREPARING 2,5-FURANDICARBOXYLIC ACID (FDCA) FROM FURFURAL

CROSS REFERENCE TO THE RELATED APPLICATIONS

This application is a continuation application of International Application No. PCT/CN2022/107071, filed on Jul. 21, 2022, which is based upon and claims priority to Chinese Patent Application No. 2022105941010, filed on May 27, 2022, the entire contents of which are incorporated herein by reference.

TECHNICAL FIELD

The present disclosure belongs to the technical field of 2,5-furandicarboxylic acid (FDCA) preparation, and specifically relates to a method for preparing FDCA with furfural as a raw material.

BACKGROUND

FDCA is an important compound for production of biomass-derived polymers such as polyester, polyurethane (PU), and polyamide (PA), and can also be used as a bio-based substitute for the bio-based raw material polyethylene terephthalate (PET). In addition, FDCA has the same number of carbon atoms as glucose, exhibits weaker aromaticity than a benzene ring, can be easily degraded, and has a wide range of applications.

Predominantly, FDCA is prepared by one of the following methods: furoic acid and an acylation reagent are subjected to an acylation reaction to obtain an intermediate 2-acyl-5-furancarboxylic acid, and then a pH is adjusted to obtain FDCA; or furan is subjected to a two-step acylation reaction to obtain FDCA. The above preparation methods require expensive raw materials and require relatively-violent reactions.

The present disclosure provides a method for preparing FDCA with furfural as a raw material, which is a brand-new preparation method. At present, there is no public technical report on preparation of FDCA with furfural as a raw material because of the aldehyde group in furfural has a high activity and is easy to undergo polymerization during acylation reactions, and thus it is difficult to obtain acylfurfural, finally resulting in an extremely-low FDCA yield.

In view of this, the present disclosure is specifically proposed.

SUMMARY

In order to solve the above defects in preparation of FDCA in the prior art, the present disclosure provides a method for preparing FDCA from furfural. The present disclosure uses inexpensive furfural as a raw material, and involves a mild reaction system, providing a novel, low-cost and safe method of preparing FDCA.

The present disclosure is implemented by the following technical solutions:

The present disclosure provides a method for preparing FDCA from furfural, including the following steps:

(1) under anhydrous conditions, mixing an acylation reagent with an ionic liquid (IL) to obtain a transparent mixed liquid A;

(2) pretreatment of the furfural: subjecting the furfural and an alcohol compound to an acetalization reaction under catalysis of an acidic ion resin to obtain an acetal compound of the furfural with the alcohol compound;

(3) under stirring, adding the acetal compound obtained in step (2) dropwise to the mixed liquid A obtained in step (1) to allow a reaction for 1 h to 2 h, adding a catalyst to continue the reaction for 3 h to 5 h, and subjecting a resulting reaction system to a post-treatment to obtain 5-acylfurfural, where because the acylation reaction is relatively easy to proceed, the catalyst is not added within the first 1 h to 2 h to avoid a violent reaction, with increased temperature, and volatilization of the raw materials, which affect the progress of the acylation reaction; and then, in order to make the acylation reaction thorough, the catalyst is added after the acylation reaction is conducted for 1 h to 2 h to make the acylation reaction complete; and (4) mixing the 5-acylfurfural obtained in step (3) with hydrogen peroxide, adding a catalyst to allow an oxidation reaction, and after the oxidation reaction is completed, subjecting a product to washing and recrystallization to obtain a white crystalline FDCA.

In the present disclosure, the furfural and alcohol compound are subjected to an acetalization reaction, such that an aldehyde group is converted into an acetal group to protect the aldehyde group, thereby avoiding a side reaction of the aldehyde group to produce a polyfurfural group during the acylation reaction.

Preferably, in step (1), a molar mass ratio of the acylation reagent to the IL is 0.1 mol:(50-60) g.

Preferably, in step (1), the acylation reagent is selected from the group consisting of acetic anhydride, acetyl chloride, and propionyl chloride; and the IL is one or more selected from the group consisting of triethylamine hydrochloride-aluminum chloride, 1-butyl-3-methylimidazolium hydrochloride, and tetrabutylammonium bromide (TBAB).

Preferably, in step (2), a molar ratio of the furfural to the alcohol compound is 1:(3-5); and the acetalization reaction is conducted at a temperature of 50° C. to 100° C. and a pressure of 0.1 MPa to 1.0 MPa.

Preferably, the alcohol compound is one or more selected from the group consisting of methanol, ethanol, and butanol; and the acidic ion resin is a sulfonic styrene resin.

Preferably, in step (3), amounts of the acetal compound and the mixed liquid A allow a molar ratio of the acylation reagent to the furfural to be 1:(1.5-3); the catalyst is added at an amount 1 wt % to 5 wt % of a mass of the acylation reagent; and the catalyst is one or more selected from the group consisting of anhydrous aluminum chloride, iron chloride, and zinc chloride.

Preferably, in step (3), the reaction is conducted at a temperature of 10° C. to 30° C. and a pressure of 0.01 MPa to 0.05 MPa, and the stirring is conducted at a rotational speed of 300 rpm to 500 rpm; and when the acetal compound is added dropwise to the mixed liquid A, a temperature rise of a resulting mixed material is controlled to be within 5° C. by adjusting a speed of the dropwise addition.

Preferably, in step (3), the post-treatment includes: extracting an acylation product in the reaction system with petroleum ether at 30° C. to 50° C. for 3 to 5 times, washing an extraction product with a 1 wt % NaOH solution at 20° C. to 30° C., and subjecting a washed product to dewatering and vacuum distillation to obtain the 5-acylfurfural, where the process of washing the extraction product with the NaOH solution can remove the catalyst for the acylation reaction, make the acetal decomposed into the original aldehyde group and alcohol to obtain 5-acylfurfural, and prevent the acetal to undergo a disproportionation reaction, which ensures a purity of the product; and the vacuum distillation is conducted at a vacuum pressure of −0.0996 MPa to −0.1 MPa and a tower pot temperature of 70° C. to 150° C.

Preferably, in step (4), the hydrogen peroxide is 20 wt % to 30 wt % hydrogen peroxide; the catalyst is copper; and the oxidation reaction is conducted at 30° C. to 45° C.

Preferably, in step (4), the catalyst is added at an amount 10 wt % of a mass of the 5-acylfurfural; and a molar ratio of the 5-acylfurfural to the hydrogen peroxide is greater than 1:1.5.

Compared with the prior art, the present disclosure has the following beneficial effects:

1. The present disclosure adopts inexpensive furfural as a raw material to prepare FDCA, resulting in excellent economic benefits.

2. In the present disclosure, an alcohol compound is used to conduct an acetalization pretreatment for furfural, such that the high-activity aldehyde group is converted into an acetal group to prevent the aldehyde group from participating in an acylation reaction, which can reduce the occurrence of side reactions; a product obtained after the acylation reaction is washed to reduce the aldehyde group while removing the catalyst; and then a mild oxidation reaction is conducted to obtain the targeted FDCA product with an improved a yield.

3. In the present disclosure, an IL is adopted as a reaction medium for an acylation reaction, rather than an organic solvent system or an aqueous solution system. This is because the IL has a strong polarity and a high boiling point that are quite different from a polarity and boiling point of the product FDCA, which is conducive to the separation of the product and can further improve a purity of the product in combination with a post-treatment.

4. In the present disclosure, the prepared 5-acylfurfural is mixed with hydrogen peroxide, and a reaction is conducted under an action of a catalyst and mild conditions to obtain the target product FDCA, which reduces energy consumption and makes the reaction simple.

DETAILED DESCRIPTION OF THE EMBODIMENTS

The technical solutions in the examples of the present disclosure are clearly and completely described below with reference to the examples of the present disclosure. Apparently, the described examples are merely a part rather than all of the examples of the present disclosure. The following description of at least one exemplary example is merely illustrative, and not intended to limit the present disclosure and application or use thereof in any way. All other examples obtained by a person of ordinary skill in the art based on the examples of the present disclosure without creative efforts shall fall within the protection scope of the present disclosure.

Unless otherwise specified, the numerical values set forth in these examples do not limit the scope of the present disclosure. The techniques and methods known to those of ordinary skill in the relevant arts may not be presented in detail, but where appropriate, the techniques and methods should be regarded as a part of the description. In all examples shown and discussed herein, any specific value should be interpreted as merely exemplary, rather than restrictive. Therefore, other examples of the exemplary examples may have different values.

Example 1

A method for preparing FDCA from furfural was provided, including the following steps:

(1) Under anhydrous conditions, 0.1 mol of acetyl chloride (an acylation reagent) was mixed with 50 g of triethylamine hydrochloride-aluminum chloride (in which a mass content of aluminum chloride was 50 wt % to 60 wt %) (an IL) in a double-row vacuum tube operating system to obtain a transparent mixed liquid A.

(2) Pretreatment of the furfural: 1 mol of the furfural was mixed with 3 mol of methanol, and an acetalization reaction was conducted at a temperature of 60° C. and a pressure of 0.5 MPa under catalysis of a sulfonic styrene resin to obtain an acetal compound of the furfural with the methanol.

(3) Under stirring, the acetal compound obtained in step (2) was added dropwise to the mixed liquid A obtained in step (1) to allow a reaction for 2 h, anhydrous aluminum chloride (a catalyst) was then added to continue the reaction for 3 h, and a resulting reaction system was subjected to a post-treatment to obtain 5-acylfurfural, where the anhydrous aluminum chloride was added at an amount 3% of a mass of acetic anhydride in the mixed liquid A.

The post-treatment was as follows: an acylation product in the reaction system was extracted with petroleum ether (with a boiling range of about 70° C.) at 50° C. for 3 to 5 times, where a volume ratio of the extraction agent (petroleum ether) to the reaction system was 1:1; and an extraction product was washed with a 1 wt % NaOH solution at 20° C. to 30° C. and then subjected to dewatering and vacuum distillation (vacuum pressure: −0.0996 MPa to −0.1 MPa, and tower pot temperature: 100° C.) to obtain 5-acetylfurfural.

Because the acylation reaction is relatively easy to proceed, the catalyst is not added within the first 2 h to avoid a violent reaction, with increased temperature, and volatilization of the raw materials, which affect the progress of the acylation reaction; and then, in order to make the acylation reaction thorough, the catalyst is added after the acylation reaction is conducted for 2 h to make the acylation reaction complete.

(4) The 5-acetylfurfural obtained in step (3) was mixed with 30 wt % hydrogen peroxide (molar ratio: 1:2), copper (a catalyst) was added at an amount 10 wt % of a mass of the 5-acetylfurfural to allow an oxidation reaction at 45° C., and after the oxidation reaction was completed, a product was subjected to washing and recrystallization to obtain a white crystal with a purity of 98.5% and a yield of 52.2%, which was the FDCA.

Example 2

A method for preparing FDCA from furfural was provided, including the following steps:

(1) Under anhydrous conditions, 0.1 mol of propionyl chloride (an acylation reagent) was mixed with 60 g of N-methyl-4-butylimidazole hydrochloride (an IL) in a double-row vacuum tube operating system to obtain a transparent mixed liquid A.

(2) Pretreatment of the furfural: 1 mol of the furfural was mixed with 5 mol of a mixture of methanol and ethanol (a molar ratio of the methanol to the ethanol was 1:1), and an acetalization reaction was conducted at a temperature of 100° C. and a pressure of 1.0 MPa under catalysis of a sulfonic styrene resin to obtain an acetal compound of the furfural with the methanol and ethanol.

(3) Under stirring, the acetal compound obtained in step (2) was added dropwise to the mixed liquid A obtained in step (1) to allow a reaction for 1 h, anhydrous aluminum chloride (a catalyst) was then added to continue the reaction for 5 h, and a resulting reaction system was subjected to a post-treatment to obtain 5-acylfurfural, where the anhydrous aluminum chloride was added at an amount 5% of a mass of acetic anhydride in the mixed liquid A.

The post-treatment was as follows: an acylation product in the reaction system was extracted with petroleum ether (with a boiling range of about 70° C.) at 30° C. for 3 to 5 times, where a volume ratio of the extraction agent (petroleum ether) to the reaction system was 0.5:1; and an extraction product was washed with a 1 wt % NaOH solution at 20° C. to 30° C. and then subjected to dewatering and vacuum distillation (vacuum pressure: −0.0996 MPa to −0.1 MPa, and tower pot temperature: 100° C.) to obtain 5-propionylfurfural.

(4) The 5-propionylfurfural obtained in step (3) was mixed with 20 wt % hydrogen peroxide (molar ratio: 1:3), copper (a catalyst) was added at an amount 10 wt % of a mass of the 5-propionylfurfural to allow an oxidation reaction at 30° C., and after the oxidation reaction was completed, a product was subjected to washing and recrystallization to obtain a white crystal with a purity of 96.8% and a yield of 49.5%, which was the FDCA.

Comparative Example 1

A preparation method in this comparative example was basically the same as the preparation method in Example 1, except that the pretreatment of furfural in step (2) was omitted; and the furfural was directly added instead of the acetal compound dropwise to the mixed liquid A in step (3).

The product FDCA obtained in Comparative Example 1 had a purity of 97.8% and a yield only of 26.5%.

In Comparative Example 1, the pretreatment of furfural is omitted, and the furfural is allowed to directly react with an acylation reagent. Because an aldehyde group in the furfural has a very high activity and is easy to undergo a polymerization reaction to produce a polyfurfural group, there are many side reactions, and only a small amount of 5-acetylfurfural can be produced, which leads to a decreased yield of the product FDCA generated by the oxidation reaction.

The objectives, technical solutions, and beneficial effects of the present disclosure are further described in detail through the above specific examples. It should be understood that the above are merely specific examples of the present disclosure, but are not intended to limit the present disclosure. Any modification, equivalent replacement, or improvement made within the spirit and principle of the present disclosure shall fall within the protection scope of the present disclosure.

What is claimed is:

1. A method for preparing 2,5-furandicarboxylic acid (FDCA) from furfural, comprising the following steps:
   (1) under anhydrous conditions, mixing an acylation reagent with an ionic liquid (IL) to obtain a transparent mixed liquid A;
   (2) pretreatment of the furfural: subjecting the furfural and an alcohol compound to an acetalization reaction under catalysis of an acidic ion resin to obtain an acetal compound of the furfural with the alcohol compound;
   (3) under stirring, adding the acetal compound obtained in step (2) dropwise to the mixed liquid A obtained in step (1) to allow a reaction for 1 h to 2 h, adding a catalyst to continue the reaction for 3 h to 5 h, and subjecting a resulting reaction system to a post-treatment to obtain 5-acylfurfural; and
   (4) mixing the 5-acylfurfural obtained in step (3) with hydrogen peroxide, adding a catalyst to allow an oxidation reaction, and after the oxidation reaction is completed, subjecting a product to washing and recrystallization to obtain a white crystal, FDCA.

2. The method for preparing FDCA from furfural according to claim 1, wherein in step (1), a molar mass ratio of the acylation reagent to the IL is 0.1 mol:(50-60) g.

3. The method for preparing FDCA from furfural according to claim 1 or 2, wherein in step (1), the acylation reagent is selected from the group consisting of acetic anhydride, acetyl chloride, and propionyl chloride; and the IL is one or more selected from the group consisting of triethylamine hydrochloride-aluminum chloride, 1-butyl-3-methylimidazolium hydrochloride, and tetrabutylammonium bromide (TBAB).

4. The method for preparing FDCA from furfural according to claim 1, wherein in step (2), a molar ratio of the furfural to the alcohol compound is 1:(3-5); and the acetalization reaction is conducted at a temperature of 50° C. to 100° C. and a pressure of 0.1 MPa to 1.0 MPa.

5. The method for preparing FDCA from furfural according to claim 4, wherein the alcohol compound is one or more selected from the group consisting of methanol, ethanol, and butanol; and the acidic ion resin is a sulfonic styrene resin.

6. The method for preparing FDCA from furfural according to claim 1, wherein in step (3), amounts of the acetal compound and the mixed liquid A allow for a molar ratio of the acylation reagent to the furfural to be 1:(1.5-3); the catalyst is added at an amount 1 wt % to 5 wt % of a mass of the acylation reagent; and the catalyst is one or more selected from the group consisting of anhydrous aluminum chloride, iron chloride, and zinc chloride.

7. The method for preparing FDCA from furfural according to claim 1, wherein in step (3), the reaction is conducted at a temperature of 10° C. to 30° C. and a pressure of 0.01 MPa to 0.05 MPa, and the stirring is conducted at a rotational speed of 300 rpm to 500 rpm; and the acetal compound is added dropwise to the mixed liquid A, wherein a temperature increase of a resulting mixed material is controlled to be within 5° C. by adjusting a dropwise addition speed.

8. The method for preparing FDCA from furfural according to claim 1, wherein in step (3), the post-treatment comprises: extracting an acylation product in the reaction system with petroleum ether at 30° C. to 50° C. for 3 to 5 times, washing an extraction product with a 1 wt % NaOH solution at 20° C. to 30° C., and subjecting a washed product to dewatering and vacuum distillation to obtain the 5-acylfurfural, wherein the vacuum distillation is conducted at a vacuum pressure of −0.0996 MPa to −0.1 MPa and a tower pot temperature of 70° C. to 150° C.

9. The method for preparing FDCA from furfural according to claim 1, wherein in step (4), the hydrogen peroxide is 20 wt % to 30 wt % hydrogen peroxide; the catalyst is copper; and the oxidation reaction is conducted at 30° C. to 45° C.

10. The method for preparing FDCA from furfural according to claim 9, wherein in step (4), the catalyst is added at an amount 10 wt % of a mass of the 5-acylfurfural; and a molar ratio of the to the hydrogen peroxide is greater than 1:1.5.

* * * * *